United States Patent
Hagiya

(10) Patent No.: US 7,485,757 B2
(45) Date of Patent: Feb. 3, 2009

(54) METHOD FOR PRODUCING 4-(METHYLTHIO) BUTANE-1,2-DIOL

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/662,522

(22) PCT Filed: Sep. 9, 2005

(86) PCT No.: PCT/JP2004/017084

§ 371 (c)(1), (2), (4) Date: Mar. 12, 2007

(87) PCT Pub. No.: WO2006/030875

PCT Pub. Date: Mar. 23, 2006

(65) Prior Publication Data

US 2007/0265474 A1    Nov. 15, 2007

(30) Foreign Application Priority Data

Sep. 14, 2004 (JP) ............................. 2004-266447

(51) Int. Cl.
*C07C 319/00* (2006.01)

(52) U.S. Cl. .......................................... 568/46; 568/18
(58) Field of Classification Search ................. 568/700, 568/300, 18, 22, 46
See application file for complete search history.

(56) References Cited

FOREIGN PATENT DOCUMENTS

| EP | 1 260 500 | * | 11/2002 |
| EP | 1 260 500 A1 | | 11/2002 |
| JP | 47-34217 | * | 11/1972 |

OTHER PUBLICATIONS

Steadman, et al., Methionine substitute. 4-Methylthiobutane-1,2-diol, Journal of Agricultural and Food Chemistry (1975), 23(6), 1137-1114.*

Steadman, Thomas R., "A Methionine Substitute: 4-Methylthiobutane-1,2-diol", J. Agric. Food Chem., vol. 23, No. 6, 1975, pp. 1137-1144.

* cited by examiner

*Primary Examiner*—Daniel M Sullivan
*Assistant Examiner*—Chukwuma O Nwaonicha
(74) *Attorney, Agent, or Firm*—Foley & Lardner LLP

(57) ABSTRACT

A method for producing 4-(methylthio)butane-1,2-diol which comprises reacting 3-butene-1,2-diol with methanethiol in the presence of an azo compound such as an azonitrile compound, an azoester compound, an azoamidine compound and an azoimidazoline compound.

2 Claims, No Drawings

METHOD FOR PRODUCING 4-(METHYLTHIO) BUTANE-1,2-DIOL

TECHNICAL FIELD

The present invention relates to a method for producing 4-(methylthio)butane-1,2-diol.

BACKGROUND ART 4-(Methylthio)butane-1,2-diol is an important compound as an intermediate of pharmaceuticals and a methionine analog (e.g. EP 338735 B and J. Agric. Food Chem., 23, 1137 (1975)). As the method for producing 4-(methylthio)butane-1,2-diol, a method comprising reacting 3-butene-1,2-diol with methanethiol in the presence of tert-butyl perphthalate and a method comprising reacting 3-butene-1,2-diol with methanethiol in the presence of a boron compound are described in J. Agric. Food Chem., 23, 1137 (1975) and EP 1260500 A, respectively.

DISCLOSURE OF THE INVENTION

The present invention provides a method for producing 4-(methylthio)butane-1,2-diol which comprises reacting 3-butene-1,2-diol with methanethiol in the presence of an azo compound.

BEST MODE FOR CARRYING OUT THE PRESENT INVENTION

As 3-butene-1,2-diol, commercially available one may be used and for example, one produced according to known methods such as a method comprising reacting 1,2-epoxy-3-butene with water in the presence of sulfuric acid catalyst (e.g. U.S. Pat. No. 5,250,743) and a method comprising isomerizing 2-butene-1,4-diol in the presence of dirhenium heptoxide (e.g. U.S. Pat. No. 5,336,815) may be used.

As methanethiol, commercially available one may be used and one produced from methanol and hydrogen sulfide. Gaseous methanethiol may be used and liquid methanethiol may be used. Liquid methanethiol can be prepared, for example, by a method comprising bringing gaseous methanethiol into a container cooled below the boiling point thereof (6° C.) to condense it.

The amount of methanethiol to be used is usually 1 mole or more relative to 1 mole of 3-butene-1,2-diol. There is no upper limit particularly and considering economical viewpoint, the amount thereof is practically 10 moles or less relative to 1 mole of 3-butene-1,2-diol.

In the present invention, the azo compound means a compound which has an azo bond (—N═N—) within the molecule and of which decomposition temperature is below 250° C. Examples thereof include an azonitrile compound such as 2,2'-azobisisobutyronitrile, 2,2'-azobis(2,4-dimethylvaleronitrile), 2,2'-azobis(2-methylbutyronitrile), 1,1'-azobis(cyclohexane-1-carbonitrile), 4,4'-azobis-4-cyanopentanoic acid, 2-phenylazo-2,4-dimethyl-4-methoxyvaleronitrile and 2-cyano-2-propylazoformamide; an azoester compound such as azobisisobutanol diacetate, methyl azobisisobutyrate and ethyl azobisisobutyrate; an azoamidine compound such as 2,2'-azobis(2-amidinopropane) dihydrochloride; an azoimidazoline compound such as 2,2'-azobis[2-(2-imidazolin-2-yl)propane]; an azoamide compound such as 1,1'-azobisformamide, 1,1'-azobis(N-methylformamide) and 1,1'-azobis(N,N-dimethylformamide); and an azoalkyl compound such as azo-tert-butane. Preferred are the azonitrile compound, the azoester compound, the azoamidine compound and the azoimidazoline compound. The commercially available azo compound is usually used.

The amount of the azo compound to be used is usually 0.001 mole or more relative to 1 mole of 3-butene-1,2-diol. There is no specific upper limit and it is practically 0.2 mole or less relative to 1 mole of 3-butene-1,2-diol considering economical viewpoint.

The reaction of 3-butene-1,2-diol and methanethiol is usually carried out in the absence of a solvent, and the reaction may be carried out in the presence of a solvent. The solvent is not particularly limited in so far as it does not prevent the reaction. Examples thereof include water; a hydrocarbon solvent such as hexane, heptane and toluene; a halogenated hydrocarbon solvent such as chlorobenzene and chloroform; an ether solvent such as diethyl ether, methyl tert-butyl ether and tetrahydrofuran; an ester solvent such as ethyl acetate; a tertiary alcohol solvent such as tert-butanol; and a nitrile solvent such as acetonitrile and propionitrile. They may be used alone or in a form of a mixture. The amount thereof to be used is not particularly limited, and it is practically 100 parts by weight or less per 1 part by weight of 3-butene-1,2-diol considering volume efficacy.

The reaction temperature differs depending on kinds of the azo compound to be used and the amount thereof, and when the reaction temperature is too low, the reaction hardly proceeds and, when the reaction temperature is too high, side reaction such as polymerization of 3-butene-1,2-diol and the product may proceed. Therefore, the reaction is usually conducted in the range of −10 to 100° C., preferably of 0 to 50° C.

The reaction is usually conducted under ordinary pressure conditions or pressurized conditions, and may be conducted under reduced pressure conditions.

The reaction of 3-butene-1,2-diol and methanethiol is usually conducted by mixing 3-butene-1,2-diol with methanethiol in the presence of the azo compound, and the mixing order is not particularly limited. When the reaction is conducted under ordinary pressure conditions, the reaction is usually conducted by a method comprising adjusting a mixture of the azo compound and 3-butene-1,2-diol at a given temperature and blowing gaseous methanethiol into them. When the reaction is conducted under pressurized conditions, the reaction is conducted, for example, by a method comprising adding the azo compound and 3-butene-1,2-diol into a container capable of sealing such as autoclave, sealing the container and pressing gaseous methanethiol into it at a given temperature, and a method comprising adding the azo compound, 3-butene-1,2-diol and liquid methanethiol into the above-mentioned sealing container, sealing the container and adjusting at a given temperature. In the case of mixing 3-butene-1,2-diol, methanethiol and the azo compound followed by adjusting at a given temperature to effect reaction or in the case of mixing 3-butene-1,2-diol with methanethiol followed by adding the azo compound thereto to effect reaction, the amount of methanethiol in the mixture containing 3-butene-1,2-diol and methanethiol is preferably 4 moles or less relative 1 mole of 3-butene-1,2-diol in order to start the reaction smoothly.

The progress of the reaction can be confirmed by a conventional analytical means such as gas chromatography, high performance liquid chromatography, thin layer chromatography, nuclear magnetic resonance spectrum analysis and infrared adsorption spectrum analysis.

After completion of the reaction, in the case of using an lipophilic azo compound, for example, 4-(methylthio)butane-1,2-diol can be isolated by removing methanethiol remained from the reaction mixture, and then, if necessary, adding water or an apolar solvent thereto, followed by extracting and concentrating the obtained aqueous layer containing 4-(methylthio)butane-1,2-diol. In the case of using a hypophilic azo compound, for example, 4-(methylthio)butane-1,2-diol can be isolated by removing methanethiol remained from the reaction mixture, and then, if necessary, adding water or a water-insoluble organic solvent thereto, followed by extracting and concentrating the obtained organic layer containing 4-(methylthio)butane-1,2-diol. Examples of the method for removing methanethiol remained from the reaction mixture include a method comprising concentrating the reaction mixture, and a method comprising blowing an inert gas such as nitrogen gas into the reaction mixture. Examples of the apolar solvent include a hydrocarbon solvent such as hexane, heptane, toluene and xylene, and the amount thereof to be used is not particularly limited. Examples of the water-insoluble organic solvent include an ester solvent such as ethyl acetate and an ether solvent such as methyl tert-butyl ether besides the above-mentioned hydrocarbon solvent, and the amount thereof to be used is not particularly limited.

EXAMPLES

The present invention will be further illustrated by Examples in detail below, but the present invention is not limited by these Examples.

Example 1

To a 100 ml flask equipped with a magnetic stirrer, 880 mg of 3-butene-1,2-diol and 10 mg of 2,2'-azobisisobutyronitrile were added. Into the mixture obtained, gaseous methanethiol was blowed at an inner temperature of 25° C. with stirring at a speed of about 10 to 20 mL/min. over 1 hour. The mixture was further stirred at the same temperature for 1 hour to effect reaction. After completion of the reaction, methanethiol remained was removed by blowing nitrogen into the reaction mixture, and 1245 mg of the oily matter containing 4-(methylthio)butane-1,2-diol was obtained. This oily matter was analyzed by gas chromatography area percentage method to find the yield of 4-(methylthio)butane-1,2-diol was 73% and 3-butene-1,2-diol was remained in 27%.

Example 2

To a 100 ml autoclave equipped with a magnetic stirrer, 1300 mg of 3-butene-1,2-diol and 20 mg of 2,2'-azobisisobutyronitrile were added. After cooling the mixture obtained at an inner temperature of 0° C., 1400 mg of liquid methanethiol was added thereto. The autoclave was sealed, and then the mixture was stirred at 30° C. for 2 hours to effect reaction. The pressure (gauge pressure) of internal autoclave at the point of starting the reaction was 2 kg/cm$^2$ and the pressure (gauge pressure) of internal autoclave at the point of completion of the reaction was 1 kg/cm$^2$. After completion of the reaction, methanethiol remained was removed by blowing nitrogen into the reaction mixture, and 1790 mg of the oily matter containing 4-(methylthio)butane-1,2-diol was obtained. This oily matter was analyzed by gas chromatography area percentage method to find the yield of 4-(methylthio)butane-1,2-diol was 67% and 3-butene-1,2-diol was remained in 33%.

Example 3

To a 100 ml autoclave equipped with a magnetic stirrer, 1300 mg of 3-butene-1,2-diol and 20 mg of azobisisobutyronitrile were added. After cooling the mixture obtained at an inner temperature of 0° C., 1400 mg of liquid methanethiol was added thereto. The autoclave was sealed, and then the mixture was stirred at 40° C. for 4 hours to effect reaction. The pressure (gauge pressure) of internal autoclave at the point of starting the reaction was 2.5 kg/cm$^2$ and the pressure (gauge pressure) of internal autoclave at the point of completion of the reaction was 0.5 kg/cm$^2$. After completion of the reaction, methanethiol remained was removed by blowing nitrogen into the reaction mixture, and 1990 mg of the oily matter containing 4-(methylthio)butane-1,2-diol was obtained. This oily matter was analyzed by gas chromatography area percentage method to find the yield of 4-(methylthio)butane-1,2-diol was 94% and 3-butene-1,2-diol was remained in 5%.

Example 4

To a 50 ml autoclave equipped with a magnetic stirrer, 2000 mg of 3-butene-1,2-diol and 20 mg of 2,2'-azobis[2-(2-imidazolin-2-yl)propane] were added. After cooling the mixture obtained at an inner temperature of 0° C., 1500 mg of liquid methanethiol was added thereto. The autoclave was sealed, and then the mixture was stirred at 40° C. for 4 hours to effect reaction. The pressure (gauge pressure) of internal autoclave at the point of starting the reaction was 2.5 kg/cm$^2$ and the pressure (gauge pressure) of internal autoclave at the point of completion of the reaction was 0.5 kg/cm$^2$. After completion of the reaction, methanethiol remained was removed by blowing nitrogen into the reaction mixture, and 10 g of ethyl acetate was added thereto to obtain the solution containing 4-(methylthio)butane-1,2-diol. The solution obtained was analyzed by gas chromatography internal standard method to find the yield of 4-(methylthio)butane-1,2-diol was 94% and 3-butene-1,2-diol was remained in 5%.

Example 5

According to a similar manner as that of Example 4, the solution containing 4-(methylthio)butane-1,2-diol was obtained except that methyl azobisisobutyrate was used in place of 2,2'-azobis[2-(2-imidazolin-2-yl)propane]. The yield of 4-(methylthio)butane-1,2-diol was 98%.

The invention claimed is:
1. A method for producing 4-(methylthio)butane-1,2-diol which comprises reacting 3-butene-1,2-diol with methanethiol in the presence of an azo compound, wherein the azo compound is an azoester compound or an azoimidazoline compound, at a temperature of from 40° C. to 50° C.
2. The method according to claim 1, wherein the azo compound is 4,4'-azobis-4-cyanopentanoic acid, 2-cyano-2-propylazoformamide, azobisisobutyrate, or 2,2'-azobis[2-(2-imidazolin-2y1)propane].

* * * * *

UNITED STATES PATENT AND TRADEMARK OFFICE
CERTIFICATE OF CORRECTION

PATENT NO.         : 7,485,757 B2
APPLICATION NO. : 11/662522
DATED              : February 3, 2009
INVENTOR(S)       : Koji Hagiya It is certified that error appears in the above-identified patent and that said Letters Patent is hereby corrected as shown below:

ON THE COVER PAGE

Item (86) the PCT Application number should read:

-- (86) PCT No.:   PCT/JP2005/017084 --

Signed and Sealed this

Seventh Day of April, 2009

JOHN DOLL
*Acting Director of the United States Patent and Trademark Office*